(12) United States Patent
Aiello et al.

(10) Patent No.: US 8,758,460 B2
(45) Date of Patent: Jun. 24, 2014

(54) CATALYST COMPOSITION

(75) Inventors: Rita Aiello, King of Prussia, PA (US);
Paul Joseph Andersen, Plymouth Meeting, PA (US)

(73) Assignee: Johnson Matthey Public Limited Company, London (GB)

( * ) Notice: Subject to any disclaimer, the term of this patent is extended or adjusted under 35 U.S.C. 154(b) by 967 days.

(21) Appl. No.: 10/473,209

(22) PCT Filed: May 22, 2003

(86) PCT No.: PCT/GB03/02233
§ 371 (c)(1),
(2), (4) Date: Dec. 13, 2004

(87) PCT Pub. No.: WO03/101612
PCT Pub. Date: Dec. 11, 2003

(65) Prior Publication Data
US 2005/0081443 A1    Apr. 21, 2005

Related U.S. Application Data

(63) Continuation-in-part of application No. 09/214,944, filed on Feb. 8, 1999, now Pat. No. 6,625,976.

(30) Foreign Application Priority Data

May 29, 2002   (GB) .................................. 0212321.4

(51) Int. Cl.
| | | |
|---|---|---|
| B01D 53/86 | (2006.01) |
| B01J 23/00 | (2006.01) |
| B01J 23/16 | (2006.01) |
| B01J 23/34 | (2006.01) |
| B01J 23/54 | (2006.01) |
| B01J 23/58 | (2006.01) |
| B01J 23/63 | (2006.01) |
| B01J 23/656 | (2006.01) |

(52) U.S. Cl.
USPC ......................................................... 48/198.3

(58) Field of Classification Search
USPC ......... 502/303, 304, 324, 325, 332, 333, 334, 502/339, 355
See application file for complete search history.

(56) References Cited

U.S. PATENT DOCUMENTS

| 4,059,675 A | 11/1977 | Yang et al. |
| 4,059,677 A | 11/1977 | Sare et al. |

(Continued)

FOREIGN PATENT DOCUMENTS

| DE | 37 40 091 A1 | 6/1989 |
| EP | 0 139 051 A1 | 5/1985 |

(Continued)

OTHER PUBLICATIONS

James J. Spivey, "Complete Catalytic Oxidation of Volatile Organics," *Ind. Eng. Chem. Res.*, vol. 26, No. 11, Nov. 1987, pp. 2165-2180.

(Continued)

*Primary Examiner* — Melvin C Mayes
*Assistant Examiner* — Douglas Call
(74) *Attorney, Agent, or Firm* — Gary D. Mangels

(57) ABSTRACT

A catalyst composition for the oxidation of carbon monoxide and volatile organic compounds and for hydrogenation reactions comprises at least two different high surface area oxide support materials wherein at least one of the high surface area support material supports at least one base metal promoter.

29 Claims, 1 Drawing Sheet

(56) References Cited

U.S. PATENT DOCUMENTS

| | | | |
|---|---|---|---|
| 4,429,155 A | 1/1984 | Göetz et al. | |
| 4,857,499 A | 8/1989 | Ito et al. | |
| 4,927,799 A | 5/1990 | Matsumoto et al. | |
| 4,956,328 A | 9/1990 | Frohning et al. | |
| 5,063,193 A | 11/1991 | Bedford et al. | |
| 5,176,897 A | 1/1993 | Lester | |
| 5,204,309 A | 4/1993 | Vorob'iev | |
| 5,254,519 A | 10/1993 | Wan et al. | |
| 5,276,249 A | 1/1994 | Greene et al. | |
| 5,292,704 A | 3/1994 | Lester | |
| 5,451,388 A * | 9/1995 | Chen et al. | 423/240 R |
| 5,578,283 A | 11/1996 | Chen et al. | |
| 5,643,545 A | 7/1997 | Chen | |
| 5,849,659 A | 12/1998 | Tanaka et al. | |
| 5,895,636 A * | 4/1999 | Nguyen et al. | 423/245.1 |
| 6,005,143 A | 12/1999 | Machado et al. | |
| 6,022,825 A * | 2/2000 | Andersen et al. | 502/303 |
| 6,051,198 A | 4/2000 | Sano et al. | |
| 6,096,278 A | 8/2000 | Gary | |
| 6,207,120 B1 | 3/2001 | Belmonte et al. | |
| 6,239,064 B1 | 5/2001 | Nguyen | |
| 2007/0259779 A1 | 11/2007 | Collier et al. | |
| 2008/0112871 A1 | 5/2008 | Obayashi et al. | |
| 2008/0226524 A1 | 9/2008 | Alive et al. | |

FOREIGN PATENT DOCUMENTS

| | | |
|---|---|---|
| EP | 0 421 878 A1 | 4/1991 |
| EP | 0 428 753 A1 | 5/1991 |
| EP | 0 547 226 A1 | 6/1993 |
| EP | 0 888 807 A1 | 1/1999 |
| EP | 1 063 002 A2 | 12/2000 |
| EP | 1 086 739 A2 | 3/2001 |
| EP | 1 199 096 A1 | 4/2002 |
| GB | 2 213 073 A | 8/1989 |
| IE | 903547 | 4/1991 |
| JP | 7-299329 A | 11/1995 |
| JP | 7-323214 A | 12/1995 |
| JP | 2000-167406 A | 6/2000 |
| WO | WO-95/11726 A1 | 5/1995 |
| WO | WO-97/18892 | 5/1997 |
| WO | WO-98/45026 | 10/1998 |
| WO | WO-01/45833 A1 | 6/2001 |
| WO | WO-03/101612 A2 | 12/2003 |
| WO | WO-2007/143837 A1 | 12/2007 |

OTHER PUBLICATIONS

J. J. Spivey et al., "Literature Review: Deactivation of Catalysts in the Oxidation of Volatile Organic Compounds," *Catalysis Today*, vol. 11, No. 4, Jan. 22, 1992, pp. 465-500.

M. Törncrona et al., "Low temperature catalytic activity of cobalt oxide and ceria promoted Pt and Pd: -influcence of pretreatment and gas composition," *Applied Catalysis B: Environmental*, vol. 14, 1997, pp. 131-145.

Francesca Zamar et al., "$CeO_2$-based Solid Solutions with the Fluorite Structure as Novel and Effective Catalysts for Methane Combustion," *J. Chem. Soc., Chem. Commun.*, 1995, pp. 965-966.

Manon M. R. Feijen-Jeurissen et al., "Mechanism of catalytic destruction of 1,2-dichloroethane and trichloroethylene over $\gamma$-$Al_2O_3$ and $\gamma$-$Al_2O_3$-supported chromium and palladium catalysts," *Catalysis Today*, vol. 54, No. 1, Nov. 26, 1999, pp. 65-79.

George R. Lester, "Catalytic destruction of hazardous halogenated organic chemicals," *Catalysis Today*, vol. 53, No. 3, Nov. 5, 1999, pp. 407-418.

G. Sinquin et al., "Perovskites as polyvalent catalysts for total destruction of $C_1$, $C_2$ and aromatic chlorinated volatile organic compounds," *Catalysis Today*, vol. 54, No. 1, Nov. 26, 1999, pp. 107-118.

\* cited by examiner

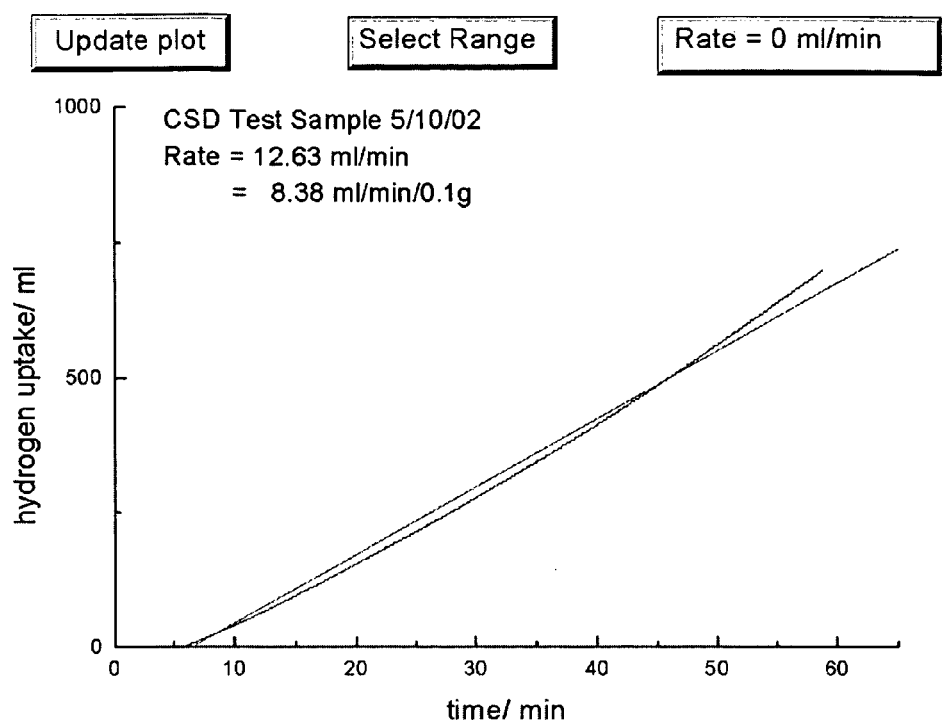

CATALYST COMPOSITION

This application is a U.S. National Phase application of International Application No. PCT/GB03/002233, and a Continuation-in-Part of U.S. patent application Ser. No. 09/214,944.

This invention relates to a catalyst composition for treating emissions from industrial and commercial processes and processes for the generation of power from hydrocarbon fuels such as coal, oil and gas. In particular the invention relates to a catalyst composition for oxidising carbon monoxide (CO) and volatile organic compounds (VOCs). The invention also relates to a catalyst composition that can be used as a heterogeneous hydrogenation catalyst in industrial reactions.

Catalytic oxidation is widely used to control VOC and CO emissions from industrial and commercial processes and power generating utilities. Typically, the process effluent is preheated and passed through a catalyst bed in the presence of excess oxygen and the components in the stream are completely oxidised to carbon dioxide ($CO_2$) and water ($H_2O$). If the effluent contains a halogenated compound, the oxidation products will include a haloacid, which can then be removed by basic scrubbing, or a halogen gas. The catalyst is the integral part of the system and may be in the form of pellets, fluidised bed particulates or monoliths.

Illustrative examples of "Volatile Organic Compounds" are saturated and unsaturated hydrocarbons, aromatic hydrocarbons, polyhalogenated derivatives thereof, such as halocarbons and dioxins and hydrocarbons containing one or more sulfur, oxygen, nitrogen or phosphorus atoms.

Conventional emission control catalysts are comprised of single or mixed metal oxides and noble metals supported on refractory oxides such as silica ($SiO_2$) or alumina ($Al_2O_3$). They may also be some combination of the two. Among the most widely used oxidation catalysts are the noble metals platinum (Pt) and palladium (Pd) supported by $Al_2O_3$. Although rhodium (Rh), ruthenium (Ru) and iridium (Ir) are also active for the oxidation of hydrocarbons, the limited supply and resulting high cost makes their use prohibitive. These noble metals are more likely to be found as minor constituents in predominantly Pt and Pd catalysts. Oxide-supported Pt and Pd catalysts are highly active for the complete oxidation of a wide variety of hydrocarbons, alcohols, ketones, and CO to $CO_2$. It is believed that the activity of Pt is due to the reduced metal [J.J. Spivey, Ind. Eng. Chem. Res. 26, 2165 (1987)], which may also be the case for Pd at low temperatures. Pt is susceptible to thermal deactivation by sintering or vaporisation of Pt metal. Pd is more resistant to sintering in oxidising environments and may therefore be preferable in some applications. In general, Pt is more active for the oxidation of saturated hydrocarbons and Pd is more active for the oxidation of unsaturated hydrocarbons and CO [J.J. Spivey et al., Catalysis Today, 11, 465 (1992)].

A variety of components can be added to increase durability under high-temperature conditions and further promote the desired reaction. For example, U.S. Pat. No. 4,857,499 describes a high-temperature Pt or Pd catalyst for use in a gas turbine combuster in which a rare earth or alkaline earth element is added to the oxide support material to prevent the oxide from sintering at high temperature. Magnesium (Mg) or silicon oxides are added to the catalyst to prevent sintering of the precious metal. This catalyst also includes a heavy metal (nickel (Ni), zirconium (Zr), cobalt (Co), iron (Fe), manganese (Mn) and corresponding oxides) to increase the concentration of activated oxygen near the precious metal particles in order to promote the desired combustion of gases. A. Törncrona et al. [Appl. Catalysis B: Environmental, 14, 131 (1997)], discuss the promoting effect of ceria (Ce) and Co on $Pt/Al_2O_3$ and $Pd/Al_2O_3$ catalysts. They observed decreases in light-off temperature of CO and propylene under both rich and lean reaction conditions when adding both pre-reduced and pre-oxidised Ce and Co. F. Zamar et al. [J. Chem. Soc., Chem. Commun., 965 (1995)], showed the methane conversion efficiency of several Ce, Zr and hafnium (Hf) oxides to be comparable to that of Pt/ceria ($CeO_2$) under similar reaction conditions. Stabilised $CeO_2$-based threeway catalysts are described in greater detail in U.S. Pat. No. 6,022,825.

Many effluent streams also contain significant quantities of halogenated solvents. Complete destruction of these compounds is important in order to avoid the formation of more hazardous compounds. However, one disadvantage to the use of supported Pt and Pd catalysts for the oxidation of halogenated VOCs is their strong interaction with Cl which severely inhibits the activity of the active metal sites. Base metal oxides offer an advantage in that they are more resistant to poisoning. The number of active metal oxide sites is far greater than the typical number of noble metal sites. In general, many oxides of the alkali and alkaline earth metals, transition metals and actinides are cheaper and more abundant than noble metals.

$Al_2O_3$ itself has been shown to be active in the destruction of chlorinated methanes, producing mostly CO and hydrogen chloride (HCl) although M.M.R. Feijen-Jeurissen et al. [Catalysis Today, 54, 65 (1999)] found $Al_2O_3$ to be much less active in the destruction of chlorinated ethanes. This same group also found they were able to achieve 95% conversion of trichloroethylene (TCE) over chromium oxide ($CrO_x$)/$Al_2O_3$ at temperatures significantly lower than those required to convert TCE over $Pd/Al_2O_3$. G.R. Lester [Catalysis Today, 53, 407 (1999)] was able to achieve 99% conversion of 1,2,4-trichlorobenzene over 20 wt % chromium (III) oxide ($CR_2O_3$)—$Al_2O_3$ and Pt—$Al_2O_3$ at temperatures of at lest 800° C., and also found the $Cr_2O_3$-containing catalyst was reported to be more active than the Pt-containing catalyst in the 500-800° C. range. Lester also compared the performance of $Cr_2O_3$—$Al_2O_3$ with several titania ($TiO_2$)-based catalysts for the destruction of halogenated VOCs and found that utilisation of the $TiO_2$-based catalyst resulted in a significant decrease in the light-off temperature of several of the compounds. The $TiO_2$-based catalysts were subsequently described in detail in U.S. Pat. Nos. 5,176,897 and 5,292,704. The formulations were based upon $TiO_2$ and experimental results that $TiO_2$ alone could convert 99% tetrachloromethane at temperatures below 300° C. Addition of vanadium pentoxide ($V_2O_5$) and tungsten oxide ($WO_3$) resulted in further improvement in benzene light off. Addition of Pt lowered the T90 of benzene and additional 50° C.

U.S. Pat. No. 6,207,120 describes an integrated treatment system for the abatement of effluent streams containing CO, VOCs or halogenated organic compounds in which a fuel is injected directly into the catalytic oxidiser unit to provide the necessary heat via combustion of the fuel. Catalysts containing $SiO_2$, $TiO_2$, alpha or gamma $Al_2O_3$, zirconia ($ZrO_2$), and $SiO_2/Al_2O_3$ and optionally at least one oxide of tungsten (W), vanadium (V) or tin (Sn) or the metals Pt, Pd or Rh are described in the patent. In one example, a mixture of hydrocarbons, aromatics and methyl bromide was oxidised to $CO_2$, water, dibromine ($Br_2$) and hydrogen bromide (HBr). U.S. Pat. No. 4,059,677 describes the use of hydrated oxides of both manganese and cobalt to promote the oxidation of chlorinated and brominated, mostly unsaturated hydrocarbons, containing 2 to 4 carbons. U.S. Pat. No. 4,059,675 describes the use of Ru on non-oxidising supports (i.e., $Al_2O_3$, $SiO_2$, iron (III) oxide ($Fe_2O_3$)) to promote the destruction of similar halogenated compounds, although they found that in contrast to Pt, Ru resulted in a mixture of gaseous halogens as well as haloacids. EP-A-1086739 describes a composite catalyst for the decomposition of exhaust gases, which catalyst comprising an organoamine compound and an iron oxide catalyst.

EP-A-1063002 describes a $V_2O_5/TiO_2$-containing catalyst and a $V_2O_5/TiO_2$—$SiO_2$-containing catalyst for the destruction of chlorotoluene and dioxin. Oxides of Mn, Co, Ni, zinc (Zn), Zr, niobium (Nb), molybdenum (Mo), Sn, tantalum (Ta), lanthanum (La) and Ce are described as alternative catalyst promoters. G. Sinquin et al. [Catalysis Today, 54, 107 (1999)] discusses the use of perovskites for the catalytic oxidation of chlorinated volatile organic compounds and compares the activity of Co and Mn-containing perovskites.

Hydrogenation is the addition of hydrogen across sterically accessible C=C, C=N and C=O double bonds and is often an important step in the preparation of pharmaceutical materials, agricultural and fine organic chemicals on a commercial scale.

U.S. Pat. No. 6,005,143 describes the use of a monolith catalyst for the hydrogenation of dinitrotoluene to toluenediamine. Examples of catalytic metals suited for the hydrogenation of dinitrotoluene are described as Group VI and VIII metals of the periodic table impregnated or directly coated onto a monolithic substrate or from a washcoat which has been deposited on the monolith. More specifically, cobalt, Raney or sponge nickel, palladium, platinum and copper are mentioned with a 10% nickel and 1% palladium on alumina composition preferred.

We have investigated known hydrogenation catalysts and catalysts for controlling VOC and CO emissions and have developed a new catalyst that is significantly more active than known base metal catalysts and has comparable activity by comparison with commercially available emission control catalysts including platinum group metals (PGM). In one embodiment the new catalyst can include some PGMs, but less are required to produce a catalyst of similar activity to known PGM emission control catalysts. Thus an advantage of the new catalyst is that it is significantly less expensive to manufacture than known PGM emission catalysts of similar activity.

According to one aspect, the invention provides a catalyst composition for the oxidation of carbon monoxide (CO) and volatile organic compounds (VOC) or for use as a hydrogenation catalyst, which composition comprising at least two different high surface area oxide support materials wherein at least one of the high surface area support material supports at least one base metal promoter.

According to a further aspect, the invention provides a catalyst composition for the oxidation of carbon monoxide (CO) and volatile organic compounds (VOC), which composition consisting of at least two different high surface area oxide support materials, wherein at least one of the high surface area support material supports at least one base metal promoter.

According to a further aspect, the invention provides a catalyst composition for the hydrogenation of a substrate, which composition consisting of at least two different high surface area oxide support materials, wherein at least one of the high surface area support material supports at least one base metal promoter.

The invention provides a catalyst composition for the oxidation of, for example, CO, hydrocarbon and halocarbon emissions from a variety of industrial and commercial processes as well as power generation applications. The catalyst is for placing in an appropriate oxidation device in which temperatures and flow rate can be controlled. An effluent stream containing, for example, CO, hydrocarbons or halocarbons can then come into contact with the catalyst facilitating conversion of the components of the effluent to $CO_2$, $H_2O$ and in the case of halocarbons, haloacid or halogen gas.

The invention also provides a catalyst composition for hydrogenation of a wide range of starting materials. Illustrative examples of reactions with which the catalyst composition of the present invention can, with utility, be used include the hydrogenation of nitroaromatic compounds e.g. dinitrotoluene to toluene diamine, nitrobenzene to aniline, para-nitrobenzoate esters to para-aminobenzoate esters, para-nitrobenzamides to para-aminobenzamides, aniline to cyclehexylamine and mononitrotoluene to toluidine; and nitrile hydrogenations, such as cyanoethylamine to aminopropylamine and cyanoethylether to aminopropylether.

The catalyst composition can be utilised over a wide range of temperatures typically encountered in the exhaust from industrial, commercial or energy-generating processes. The primary advantage of the invention over known emission control catalysts is that the catalyst can function effectively in the absence of precious metal. Results of recent testing show that the performance of an embodiment of the invention consisting of manganese and ceria base metal catalyst promoters supported on Zr-stabilised Ce and La-stabilised $Al_2O_3$ is comparable to several commercial catalysts which contain a considerable amount of precious metal. The reduction of the amount of precious metal in the catalyst should result in significant cost savings compared to the conventional precious metal catalysts.

A second advantage of this embodiment of the present invention is that Ce and Mn are used as base metal catalyst promoters rather than much more toxic elements, such as V and chromium (Cr) which have been used in the past. Use of the more toxic additives requires safety precautions which add cost to the manufacture of the product.

Each high surface area support material can be chosen from the group consisting of $CeO_2$, perovskites, nickel oxide (NiO), manganese dioxide ($MnO_2$), praseodymium (III) oxide ($Pr_2O_3$), $TiO_2$, $SiO_2$, $Al_2O_3$, $ZrO_2$ and, a composite oxide or a mixed oxide of any two or more thereof. In one embodiment at least one high surface area support material is stabilised. The or each stabilisers can be selected from at least one transition element, such as at least one of Zr, La, aluminium (Al), yttrium (Y), praseodymium (Pr) or neodymium (Nd) or an oxide thereof or a composite oxide or a mixed oxide of any two or more thereof, or at least one alkaline earth metal, e.g. barium (Ba). For the avoidance of doubt, where each high surface area support material is stabilised, the stabilisers can be the same or different.

"Composite oxide" as defined herein means a largely amorphous oxide material comprising oxides of at least two elements which are not true mixed oxides consisting of the at least two elements.

Where a high surface area support material is $Al_2O_3$, it can be in the form of alpha-, gamma-, beta-, delta- or theta-$Al_2O_3$, for example.

In one illustrative embodiment one high surface area support material is Zr-stabilised $CeO_2$. The Zr-stabilised $CeO_2$ can contain from about 2 to about 50% $ZrO_2$. For example, about 58% by weight $CeO_2$ and about 42% by weight $ZrO_2$.

In another illustrative embodiment one high surface area support material is La-stabilised $Al_2O_3$. The La-stabilised $Al_2O_3$ can contain from about 2 to about 7% by weight lanthanum oxide.

In another illustrative embodiment, the high surface area support materials according to the present invention comprise La-stabilised $Al_2O_3$ and Zr-stabilised $CeO_2$.

In another illustrative embodiment, each high surface area support material has a mean particle size of less than about 20 µm, such as a mean particle size of about 5 µm. This is because when making the catalyst composition it is desirable that each high surface area support material is of sufficiently large particle size so as to prevent each catalyst support material from forming a solution or a sol with the liquid medium of the slurry The or each at least one base metal catalyst promoter can be selected from at least one of Nd, Ba, Ce, La, Pr, Mg, calcium (Ca), Mn, Co, Ni, Zn, Nb, Zr, Mo, Sn, Ta or strontium (Sr). In one illustrative embodiment, for example, the base metal catalyst promoters are Ce and Mn.

In a further illustrative embodiment, the catalyst composition according to the present invention comprises at least one PGM. This can be at least one of Pt, Pd, Rh, Ru and Ir.

The catalyst composition according to the invention can be supported on a substantially inert substrate material comprising a flow through monolith, such as a ceramic or metal honeycomb structure. Alternatively, the substrate can comprise particles such as spheres, pellets or short extruded segments of a suitable refractory material.

According to a further aspect, the invention provides a method of oxidising at least one of carbon monoxide and volatile organic compounds in a fluid, which method comprising contacting the fluid with the catalyst composition according to the invention. The fluid can be a gas emitted from industrial, commercial or energy-generating processes.

According to a further aspect, the invention provides a method of hydrogenating at least one substrate in a fluid, which method comprising contacting the fluid with the catalyst composition according to the invention.

According to a further aspect, the invention provides a method of making a catalyst composition according to the invention, which method comprising:
(a) forming on a non-porous substrate a combined washcoat of a first high surface area support material and a second high surface area support material from a slurry in which each of the high surface area support materials is of sufficiently large particle size so as to prevent each catalyst support material from forming a solution or a sol with the liquid medium of the slurry; and
(b) impregnating at least one base metal catalyst promoter into each catalyst support material either before or after formation of the washcoat on the non-porous substrate, the amounts of first and second high surface area support materials present in the catalyst composition being determined by the amount of base metal required in each high surface area support material and the respective incipient water absorption capability of each high surface area support material.

The catalyst composition can comprise two high surface area support materials, exemplified by Zr-stabilised Ce and La-stabilised $Al_2O_3$, although unstabilised $Al_2O_3$ may be used. The at least one base metal catalyst promoter (exemplified by Mn and Ce) are split between the two support materials. In one embodiment of the invention, the base metal catalyst promoters are impregnated from an aqueous solution into the washcoat consisting of a mixture of the two support materials and the way in which the base metal catalyst promoters are split between the two support materials depends on the fraction of the aqueous impregnation solution absorbed by the respective support materials. For example, if it is required that 50% of the available Mn and Ce is to be supported on the Zr-stabilised $CeO_2$ and the other 50% of available Mn and Ce is to be supported on the La-stabilised $Al_2O_3$ then the washcoat would be formulated so that the water absorption of the Zr-stabilised $CeO_2$ in the catalyst composition (i.e. (ml water absorbed/g)×(g in catalyst)) is equal to the water absorption of the La-stabilised $Al_2O_3$ in the catalyst composition. Thus, the ratio of the support materials is specified by their relative water absorptions and the absolute amounts of the support materials is specified by the amount of support needed in the catalyst composition (more specifically, a certain amount of Zr-stabilised $CeO_2$ may be needed for adequate performance). The desired split of the Mn and Ce depends on the duty required of the catalyst composition. In some applications, equal amounts of first and second high surface area support material is required. In other applications, more first high surface area support material than second high surface area support material is needed (or vice versa). For example, catalyst compositions having manganese and cerium split ranging from (a) 27% of Mn and Ce as Mn/Ce/Zr—$CeO_2$-73% of Mn and Ce as Mn/Ce/La—$Al_2O_3$ to (b) 73% of Mn and Ce as Mn/Ce/Zr—$CeO_2$-27% of Mn and Ce as Mn/Ce/La—$Al_2O_3$ have been prepared according to the methods of the invention. A similar method can be used for selectively distributing PGMs between the first and second high surface area support materials.

In an alternative method of making the catalyst composition, a portion of the total manganese and cerium is impregnated into a bulk form of the first support material and the remaining portion of the manganese and cerium is impregnated into a bulk form of the second support material prior to the formation of the washcoat slurry. Since the impregnated base metal catalyst promoter is essentially insoluble in the washcoat it remains interacted with its associated support material in the final catalyst composition. In this embodiment also, the ratio of the two oxide support materials is chosen on the basis of their relative water absorptions and the desired split between the Mn and Ce intimately interactive with, for example, Zr-stabilised $CeO_2$ and the Mn and Ce intimately interactive with La-stabilised $Al_2O_3$.

In order that the invention may be more fully understood, reference is made to the accompanying Examples by way of illustration only and by reference to the sole accompanying drawing which is a graph showing hydrogen uptake vs. time in the hydrogenation of nitrobenzene to aniline over a catalyst composition according to the invention.

EXAMPLE 1

In this embodiment, Zr-stabilised $CeO_2$ is slurried with La-stabilised gamma $Al_2O_3$. This mixture is then dried at 60° C. and fired at 500° C. to attain further stabilisation. An aqueous solution of cerium nitrate ($Ce(NO_3)_2$) is then added to the resulting material. The impregnated material is then dried at 60° C. and fired at 500° C. An aqueous solution of manganese nitrate ($Mn(NO_3)_2$) is then added to the resulting material. The impregnated material is then dried at 60° C. and fired at 500° C. The steps of impregnating the high surface area support material first with the Ce catalyst promoter before the Mn catalyst promoter can, of course, be reversed.

Precious metal, such as Pt, Pd or Rh can also be impregnated on the resulting materials, if desired.

EXAMPLE 2

The performance of the catalyst composition of Example 1 for CO, hydrocarbon and halocarbon conversion was compared with two commercially available PGM-containing emission control catalysts using methods familiar to the skilled person. The first commercially available catalyst (comparative catalyst A) consists of Pt, Pd and Mn supported on $Al_2O_3$. The second commercially available catalyst (comparative catalyst B) is a VOC oxidation catalyst consisting of Pt on $Al_2O_3$.

A preparation of each catalyst was coated on a 400 cells per square inch (62 cells $cm^{-2}$) ceramic monolith and 1" diameter×2" length core samples were cut from this for testing. Each core was placed in a gas stream of a laboratory test rig, which gas containing CO, hydrocarbons, water or halocarbon in excess oxygen according to test conditions 1 or 2 set out in Table 1 and at a total flow rate of 6 L/min. Test condition 1 is designed to simulate that of an exhaust gas from a representative chemical manufacturing process. Test condition 2 represents the exhaust from a lean-burn natural gas engine.

Samples of gas were taken at the outlet of the core and analysed using a gas chromatograph equipped with flame ionisation detection (FID). Three samples of gas were taken at each temperature and the results were averaged. Conversion was then calculated at a series of temperatures from the inlet and outlet concentrations.

TABLE 1

Details of test conditions and synthetic gas composition

| Synthetic gas component/conditions | Test condition (1) | Test condition (2) |
|---|---|---|
| CO | 1000 ppm | 500 ppm |
| Hydrocarbon | 150 ppm methane ($CH_4$) | 500 ppm ethane ($C_2H_6$) as C1 |
| Methyl acetate | 300 ppm | — |
| Benzene | 10 ppm | — |
| Methyl bromide (MeBr) | 30 ppm | — |
| NOx | — | — |
| Water | 67% | — |
| Oxygen ($O_2$) | 5% | 2% |
| Dinitrogen ($N_2$) | Balance | Balance |
| Pressure | 150 pressure per square inch gauge (psig) | 15 psig |

The catalyst of Example 1 and comparative catalyst A were tested fresh under test condition (1) in Table 1. The conversion efficiencies of the catalysts obtained are summarised in Table 2. Conversion is represented by T75, the temperature at which 75% of the specific gas is converted. Values in Tables 1 and 2 after PGM-containing catalysts are details of the PGM loading. The ratios are for Pt:Pd:Rh and the value after the ratio is the total PGM loading in g $ft^{-3}$.

TABLE 2

Conversion efficiencies under test condition 1.

| Catalyst | T75 benzene | T75 MeBr |
|---|---|---|
| Comparative catalyst A, 1:20:0/210 | 375 | 310 |
| Comparative catalyst A with Ce, 1:20:0/210 | 358 | 310 |
| Catalyst of Example 1 (PGM) 1:20:0/210 | 330 | 310 |
| Catalyst of Example 1 (PGM) 1:3:0/160 | 345 | 325 |
| Catalyst of Example 1 (no PGM) | 360 | 330 |

The data in Table 2 shows that the catalyst of Example 1 provides benzene and MeBr conversion which is comparable to that of commercial product consisting of Pt/Pd/Mn on $Al_2O_3$, even without PGM.

TABLE 3

Conversion efficiencies under test condition 2.

| Catalyst | T75 CO | T75 $C_2H_6$ | CO conversion at 550° C. | $C_2H_6$ conversion at 550° C. |
|---|---|---|---|---|
| Comparative catalyst B, 1:0:0/40 | 173 | 535 | 100 | 82 |
| Catalyst of Example 1 (PGM) 1:3:0/160 | 142 | 397 | 99 | 98 |
| Catalyst of Example 1 (no PGM) | 212 | 457 | 99 | 94 |

The results show that the catalyst of Example 1 (no PGM) can achieve 75% conversion of CO at a temperature within 40° C. of that of a commercial product consisting of Pt on $Al_2O_3$. The catalyst of Example 1 (no PGM) can also achieve conversion of $C_2H_6$ at a significantly lower temperature than the commercial product. At the exhaust temperature of a typical natural gas engine this catalyst can achieve the required destruction efficiency of CO and $C_2H_6$.

Accordingly, the catalyst of Example 1 has been shown to be effective in the range 200° C.-500° C.

EXAMPLE 3

The performance of the catalyst composition of Example 1 impregnated with palladium for hydrogenation was demonstrated via the hydrogenation of nitrobenzene to aniline. The catalyst was prepared as an unsupported powder containing 1.75 wt. % Pd. A 0.1508 g sample of catalyst was placed in a glass-lined stainless steel reactor and 45 ml of nitrobenzene solution (6 percent nitrobenzene in methanol) was added under nitrogen. The reactor was then sealed and placed in a heating mantle that was maintained at 170° C. When the temperature of the reaction medium attained 40° C., the reactor was purged with nitrogen for 30 seconds. The reactor was then purged with hydrogen (at a pressure of 2 bar, gauge) three times. During the reaction, the temperature of the reactor and hydrogen pressure in the reactor were kept at 40° C. and 2 bar, respectively.

The agitator was then turned on at 1200 rpm. This allowed the catalyst to simultaneously contact nitrobenzene and hydrogen and initiated the reaction. Hydrogen was consumed as the reaction proceeded. Hydrogen pressure in the reactor was monitored and hydrogen was continually replenished, keeping the pressure constant. Flow to the reactor was recorded during this time and the rate of nitrobenzene hydrogenation was reported as the rate of hydrogen uptake. The reaction was discontinued after 59 minutes by stopping the agitator. The rate of nitrobenzene hydrogenation was 83.75 ml/min/g catalyst. FIG. 1 shows the hydrogen uptake in the hydrogenation of nitrobenzene to aniline over the catalyst.

The invention claimed is:

1. A method for controlling carbon monoxide (CO) and a volatile organic compound emissions comprising:
   a. contacting a fluid emission comprising at least one of carbon monoxide (CO) and a volatile organic compound selected from the group consisting of saturated and unsaturated hydrocarbons, aromatic hydrocarbons, halocarbons, dioxins, and hydrocarbons containing one or more of sulfur, oxygen, nitrogen, and phosphorous, with a washcoat that contains an oxidation catalyst, wherein said washcoat is free of platinum group metals and is deposited on a substrate; and
   b. oxidizing the carbon monoxide and/or volatile organic compound in the presence of the oxidation catalyst to form at least one of $CO_2$, $H_2O$, haloacid, or halogen gas;

wherein said oxidation catalyst comprises a composite oxide having at least two different high surface area oxide support materials, and
    i. the at least two different high surface area oxide support materials are selected from the group consisting of $CeO_2$, NiO, $CaTiO_3$, $MnO_2$, $Pr_2O_3$, $TiO_2$, $SiO_2$, $Al_2O_3$, and $ZrO_2$,
    ii. at least one of the oxide support materials is impregnated with at least one promotion metal selected from the group consisting of Nd, Ba, Ce, La, Pr, Mg, Ca, Mn, Co, Zn, Nb, Zr, Mo, Sn, Ta, and Sr, and
    iii. each of the at least two different high surface area oxide support materials has a mean particle size of about 5 μm to about 20 μm.

2. The method of claim 1, wherein at least one of the oxide support materials is stabilized with at least one metal selected from the group consisting of Zr, La, Al, Y, Pr, Nd, Ba, and oxides thereof.

3. The method of claim 2, wherein said metal is Ce, Mn, or both Ce and Mn.

4. The method of claim 1, wherein at least one of said oxide support materials is $CeO_2$ or $Al_2O_3$.

5. The method of claim 1, wherein the oxide support materials are $CeO_2$ and $Al_2O_3$.

6. The method of claim 5, wherein said metal is Ce, Mn, or both Ce and Mn.

7. The method of claim 5, wherein said metal is both Ce and Mn.

8. The method of claim 1, wherein the oxide support materials are Zr-stabiliz $CeO_2$ and La-stabilized $Al_2O_3$.

9. The method of claim 1, wherein said metal is Ce, Mn, or both Ce and Mn.

10. The method of claim 7, wherein said substrate is a flow-through monolith and wherein said oxidation catalyst is wherein said fluid is an exhaust gas emitted from power generation using hydrocarbon fuels.

11. The method of claim 1, wherein said substrate is non-porous.

12. The method of claim 1, wherein said substrate is a flow-through monolith.

13. The method of claim 1, wherein said fluid emission is an exhaust gas emitted from power generation using hydrocarbon fuels.

14. A method for controlling carbon monoxide (CO) and a volatile organic compound emissions comprising:
    a. contacting a fluid comprising at least one of carbon monoxide (CO) and a volatile organic compound selected from the group consisting of saturated and unsaturated hydrocarbons, aromatic hydrocarbons, halocarbons, dioxins, and hydrocarbons containing one or more of sulfur, oxygen, nitrogen, and phosphorous, with a washcoat that contains an oxidation catalyst that is deposited on a substrate; and
    b. oxidizing the carbon monoxide and/or volatile organic compound in the presence of the oxidation catalyst to form at least one of $CO_2$, $H_2O$, haloacid, or halogen gas;
wherein said oxidation catalyst comprises a composite oxide having at least two different high surface area oxide support materials, wherein
    i. the at least two different high surface area oxide support materials are selected from the group consisting of $CeO_2$, NiO, $CaTiO_3$, $MnO_2$, $Pr_2O_3$, $TiO_2$, $SiO_2$, $Al_2O_3$, and $ZrO_2$, and
    ii. at least one of the oxide support materials is impregnated with at least one promotion metal selected from the group consisting of Nd, Ba, Ce, La, Pr, Mg, Ca, Mn, Co, Zn, Nb, Zr, Mo, Sn, Ta, and Sr,
    wherein the catalyst is formed without the addition of a platinum group metal to the oxides in the catalyst.

15. The method of claim 14, wherein each of the at least two different high surface area oxide support materials has a mean particle size of about 5 μm to about 20 μm.

16. The method of claim 14, wherein said composite oxide consists essentially of two different high surface area oxide support materials, wherein at least one of the oxide support materials is promoted with at least one metal selected from the group consisting of Nd, Ba, Ce, La, Pr, Mg, Ca, Mn, Co, Zn, Nb, Zr, Mo, Sn, Ta, and Sr.

17. The method of claim 14, wherein at least one of the oxide support materials is stabilized with at least one metal selected from the group consisting of Zr, La, Al, Y, Pr, No, Ba, and oxides thereof.

18. The method of claim 14, wherein at least one of said oxide support materials is $CeO_2$ or $Al_2O_3$.

19. The method of claim 14, wherein the composite oxide consists essentially of metal promoted $CeO_2$ and $Al_2O_3$.

20. The method of claim 19, wherein the oxide support materials are Zr-stabilized $CeO_2$ and La-stabilized $Al_2O_3$.

21. The method of claim 19, wherein said metal is Ce, Mn, or both Ce and Mn.

22. The method of claim 19, wherein said metal is both Ce and Mn.

23. The method of claim 14, wherein said metal is Ce, Mn, or both Ce and Mn.

24. The method of claim 14, wherein said composite oxide consists essentially of about 27-73% Mn/Ce/Zr—$CeO_2$ and from about 73 to 27% Mn/Ce/La—$Al_2O_3$.

25. The method of claim 14, wherein said composite oxide consists of about 27-73% Mn/Ce/Zr—$CeO_2$ and from about 73 to 27% Mn/Ce/La—$Al_2O_3$.

26. The method of claim 25, wherein said substrate is a flow-through monolith and wherein said oxidation catalyst is wherein said fluid is an exhaust gas emitted from power generation using hydrocarbon fuels.

27. The method of claim 14, wherein said substrate is non-porous.

28. The method of claim 14, wherein said substrate is a flow-through monolith.

29. The method of claim 14, wherein said fluid is an exhaust gas emitted from power generation using hydrocarbon fuels.

* * * * *